United States Patent [19]

Takahashi

[11] 4,248,506
[45] Feb. 3, 1981

[54] EYE FUNDUS OBSERVING OPTICAL SYSTEM

[75] Inventor: Fumio Takahashi, Yokohama, Japan

[73] Assignee: Nippon Kogaku K.K., Tokyo, Japan

[21] Appl. No.: 973,877

[22] Filed: Dec. 28, 1978

[30] Foreign Application Priority Data

Dec. 28, 1977 [JP] Japan .......................... 52/159447

[51] Int. Cl.³ .............................................. A61B 3/10
[52] U.S. Cl. .......................................... 351/6; 350/54
[58] Field of Search ...................... 350/46, 47, 38, 54; 351/6, 7

[56] References Cited

U.S. PATENT DOCUMENTS

| 3,089,398 | 5/1963 | Wilms | 351/7 X |
| 3,259,039 | 7/1966 | Okajima | 351/7 |
| 3,925,793 | 12/1975 | Matsumura et al. | 351/6 X |
| 4,068,932 | 1/1978 | Ohta et al. | 351/7 |
| 4,102,563 | 7/1978 | Matsumura et al. | 351/7 |

FOREIGN PATENT DOCUMENTS 1361665  4/1964  France ........................ 351/7

*Primary Examiner*—Paul A. Sacher
*Attorney, Agent, or Firm*—Shapiro and Shapiro

[57] ABSTRACT

An eye fundus observing optical system which can perform the diopter correction of the inner focus type by the construction that a relay lens system for forming a second fundus image from a first fundus image formed by an objective lens is constituted by two first and second positive lenses, and the front focus of the first lens is coincident with the back focus of the objective lens, and the second lens is movable in the direction of the optic axis. Further, in accordance with the diopter of the eye to be examined, the second lens is moved in the direction of the optic axis.

3 Claims, 2 Drawing Figures

EYE FUNDUS OBSERVING OPTICAL SYSTEM

BACKGROUND OF THE INVENTION

1. Field of the Invention

This invention relates to an optical system for observing or photographing therethrough the fundus of an eye, and more particularly to an optical system for effecting the correction of the diopter of an eye to be examined.

2. Description of the Prior Art

For the purpose of observing or photographing an eye fundus and correcting the diopter of the eye, there are known the inner focus type and the outer focus type devices. In a device based on the so-called outer focus type method wherein the position of the fundus image is varied by the diopter of the examiner, a telecentric system is used for the optical system to eliminate variation in image height and the construction is relatively simple. However, the position of the image is varied to thereby vary the length of the lens barrel and this is not preferable. For example, in case of a so-called fundus camera which is chiefly directed to photographing, the camera portion must be movable by means of bellows or the like and this leads to a larger size of the entire device and accordingly to poor operability. In case of a portable eye examining device, compactness and light weight must be given priority and the outer focus type is not appropriate. On the other hand, unlike the outer focus type, in the inner focus type wherein the position of the fundus image is kept fixed, the optical system itself is complicated making it difficult to provide a compact and light-weight device.

SUMMARY OF THE INVENTION

It is an object of the present invention to provide an eye fundus observing optical system which can perform the diopter correction of the inner focus type by a simple construction.

In the eye fundus observing optical system of the present invention, a relay lens system for forming a second fundus image from a first fundus image formed by an objective lens is constituted by two first and second positive lenses, and the front focal point of the first lens is coincident with the back focal point of the objective lens, and the second lens is movable in the direction of the optic axis. Further, in accordance with the diopter of the eye to be examined, the second lens is moved in the direction of the optic axis to thereby effect diopter correction.

The invention will become more fully apparent from the following detailed description thereof taken in conjunction with the accompanying drawings.

DESCRIPTION OF THE PREFERRED EMBODIMENTS

Figure 1:
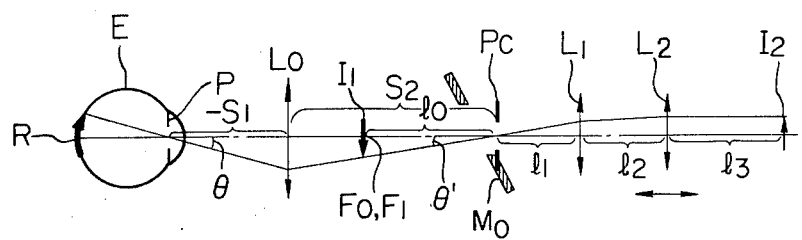
FIG. 1 shows the construction of the eye fundus observing optical system according to the present invention and the manner in which an eye fundus image is formed when the eye to be examined is in emmetropia.

The construction of the present invention will hereinafter be described in detail by the use of FIG. 1. FIG. 1 shows the construction of the diopter correcting optical system according to the present invention and also shows the manner in which the image of an eye fundus is formed when the eye E to be examined is in a condition of emmetropia (0.00 diopter).

The light from the fundus R of the eye E to be examined passes through a pupil P and a first image $I_1$ of the eye fundus is formed by means of an objective lens $L_0$. This first fundus image $I_1$ is formed at the position of the back focus $F_0$ of the objective lens $L_0$ when the eye E to be examined is in a condition of emmetropia, and varies its position on the optic axis as well as the size thereof in accordance with the diopter of the eye E to be examined. A diaphragm lies at a position conjugate with the pupil P with respect to the objective lens $L_0$, and is formed as an apertured mirror $M_o$ having an unshown illuminating optical system obliquely disposed for illuminating the eye fundus. To enhance the effect of this diaphragm $M_o$, a diaphragm $P_C$ is provided adjacent to the obliquely disposed, apertured mirror $M_o$. The light from the first fundus image $I_1$ further passes through the diaphragm $P_C$ and a second image $I_2$ of the eye fundus is formed by means of a relay lens system comprising a first lens $L_1$ and a second lens $L_2$ movable in the direction of the optic axis. Here, the front focal point $F_1$ of the first lens $L_1$ is coincident with the back focal point $F_0$ of the objective lens $L_0$. Also, when the eye E to be examined is in emmetropia, the second lens $L_2$ is disposed so that the front focal point of the relay lens system, namely the front focal point of the combined first and second lens system, is coincident with the position of the diaphragm $P_C$, and the relay lens system forms a telecentric system. The position of the second lens at this time is the reference position for the diopter correction.

How to achieve the diopter correction by the movement of the second lens in such a construction will hereinafter be described in detail.

Let $f_0$, $f_1$ and $f_2$ be the focal lengths of the objective lens $L_0$, the first lens $L_1$ and the second lens $L_2$, respectively. The intervals between the components are determined as follows, on the assumption that the lenses are all thin systems.

Distance between the pupil P of the eye to be examined and the objective lens $L_0$:$S_1$ Distance between the objective lens $L_0$ and the diaphragm $P_C$:$S_2$ Distance between the first fundus image $I_1$ and the diaphragm $P_C$:$l_0$ Distance between the diaphragm $P_C$ and the first lens $L_1$:$l_1$ distance between the first lens $L_1$ and the second lens $L_2$ lying at the reference position: $l_2$ Distance between the second lens $L_2$ lying at the reference position and the second fundus image $I_2$:$l_3$ Now, in FIG. 1, the first fundus image $I_1$ is varied both in position and in size by the diopter of the eye E to be examined being varied, and if the size of the first fundus image $I_1$ at this time is $y_1$, and the distance thereof from the diaphragm $P_C$ is $l_0$, then the following relation is established:

$$\frac{y_1}{l_0} = \theta' \; (\equiv \text{constant}) \tag{1}$$

In case of the outer focus type, the second fundus image $I_2$ is also moved with the movement of the first fundus image $I_1$. Accordingly, the condition for effecting the diopter correction of the inner focus type by moving the second lens $L_2$ is obtained as the condition in which equation (1) is always established even if the second lens $L_2$ is moved from the reference position when the second fundus image $I_2$ is regarded as a fixed object on the basis of the principle of reversibility of light rays and the image of this fixed object is regarded as being formed at the position of the fundus image $I_1$.

Since the first fundus image and the second fundus image are conjugate with each other even when the second lens $L_1$ is moved by an amount X from the reference position (for the diopter correction), if $y_2$ is the size of the second fundus image, the following is established by the expression of the so-called Gaussian bracket:

$$[-(l_0+l_1),\psi_1,-(l_2+x),\psi_2,-(l_3-x)]=0 \quad (2)$$

$$\frac{y_1}{y_2} = \frac{1}{[\psi_1' - (l_2 + x),\psi_2' - (l_3 - x)]} \quad (3)$$

where $$\psi_1 + \frac{1}{f_2} \text{ and } \psi_2 \frac{1}{f_2}.$$

The method of expression of the Gaussian bracket such as [..., ..., ...] is described in detail in an article entitled "Gaussian Optics and Gaussian Brackets" by M. Herzberger (Journal of Optical Society of America, Vol. 33, 1943, pp. 651–655). From equation (2), $$l_0 = \frac{[-l_1 \cdot \psi_1' - (l_2 + x), \psi_2' - (l_3 - x)]}{[\psi_1' - (l_2 + x), \psi_2' - (l_3 - x)]} \quad (2)'$$

From equations (3) and (2)', equation (1) may be rewritten thus:

$$\frac{y_1}{l_0} = \frac{y_2}{[-l_1 \cdot \psi_1' - (l_2 + x), \psi_2' - (l_3 - x)]} \quad (4)$$

The size $y_2$ of the second fundus image $I_2$ is constant because it is predetermined by the field number of an unshown eyepiece for observing this image therethrough and the film size. Therefore, obtaining the condition for the diopter correction by the movement of the second lens $L_2$ is ascribable to the problem of obtaining the condition in which the value of the denominator in equation (4) is constant irrespective of the value of x. Rearranging the denominator of equation (4), it becomes a quadratic equation with respect to x, and the coefficient A of $x^2$ is $$A+\psi_2 \cdot [-l_1,\psi_1] \quad (5)$$

and the coefficient B of x is $$B=(l_3-l_2) \cdot \psi_2 \cdot [-l_1,\psi_1]-l_1 \cdot \psi_2 \quad (6)$$

Therefore, the condition for the value of the denominator to be constant irrespective of x is given by a condition in which $A=B=0$ is established.

If $A=0$ in equation (5), this means that the front focal point $F_1$ of the first lens $L_1$ is positioned at the diaphragm $P_C$, which in turn means that a telecentric system is formed only by the first lens $L_1$ and in this case, the construction is the same as the conventional outer focus type. On the other hand, a relation is newly derived to obtain the condition of $B=0$ in equation (6). That is, the relay lens system comprising a combination of the first lens $L_1$ and the second lens $L_2$ forms a telecentric system when the second lens $L_2$ is at the reference position, whereby the following equation is established:

$$[-l_1,\psi_1,-l_2,\psi_2]=0 \quad (7)$$

Also, as regards the total focal length $f_{12}=1/\psi_{12}$ of the relay lens system, the following relation is established:

$$\psi_{12}=[\psi_1,-l_2,\psi_2] \quad (8)$$

From equations (7) and (8), $l_1$ and $l_2$ may be obtained:

$$l_1 = \frac{1}{\psi_{12} \cdot \psi_1}(\psi_{12} - \psi_2) \quad (9)$$

$$l_2 = -\frac{1}{\psi_1 \cdot \psi_2}(\psi_{12} - \psi_1 - \psi_2) \quad (10)$$

If these are placed into equation (6) and if $B=0$, the following is obtained:

$$f_2=l_3 \quad (11)$$

This is a condition for the second lens $L_2$ and from this, the condition for the first lens $L_1$ is obtained. Even when the diopter correction is not necessary, namely, when the second lens $L_2$ is at the reference position, the first fundus image $I_1$ and the second fundus image $I_2$ are in conjugate relationship, so that the following is established:

$$[-(l_0+l_1),\psi_1,-l_2,\psi_2,-l_3]=0 \quad (12)$$

By this equation (12), the following condition for the first lens $L_1$ may be obtained if equations (9) and (10) are used:

$$f_1=l_0+l_1 \quad (13)$$

Here, the following relation is established from Newton's formula regarding the objective lens $L_0$:

$$l_0=-\beta_0 \cdot f_0$$

where $\beta_0$ is the magnification of the projection of the pupil P onto the diaphragm $P_C$ by the objective lens $L_0$ and may be expressed as $$\beta_0 = \frac{s_2}{s_1}.$$

Therefore, from equation (13), the following condition for the first lens $L_1$ and the objective lens $L_0$ is given:

$$f_1=l_1-\beta_0 \cdot f_0 \quad (14)$$

The condition of equation (14) thus obtained is a condition for only the primary coefficient B of the x of the denominator in equation (4) to be zero and does not satisfy the condition of equation (1) for completely achieving the diopter correction. However, in the construction which satisfies equation (14), the relation between the amount of movement of the second lens $L_2$ and the size $y_2$ of the second fundus image $I_2$ is given thus:

$$y_2 = \frac{f_0 \cdot f_2 \cdot \tan\theta}{f_1}\left(1 + \frac{x^2}{f_2^2}\right) \qquad (15)$$

where $\theta$ is the half angle of view of the objective lens $L_0$. Since the amount of movement of the second lens necessary for the diopter correction is generally small, the size of the image is varied only slightly. Actually, even if the diopter of the eye to be examined is ±20D (diopter), $x = \pm 8$ mm when, for example, $f_2 = 54$ mm, and $x^2/f_2^2 = 0.022$ and thus, $y_2$ is only varied by about 2%. Therefore, only if equation (14) is satisfied, diopter correction sufficient in practice becomes possible.

A construction satisfying equation (14), as is apparent from equation (13) and FIG. 1, is obtained when the front focus $F_1$ of the first lens $L_1$ coincides with the back focus $F_0$ of the objective lens $L_0$.

On the other hand, independently of the condition of equation (14), the focal length $f_{12}$ of the relay lens system comprising a combination of the first lens $L_1$ and the second lens $L_2$ is represented as:

$$f_{12} = \frac{-\beta_0 y_2}{\tan\theta} \qquad (16)$$

The angle of view $2\theta$ is a value peculiar to the objective lens $L_0$, and $\beta_0$ is also determined by the objective lens $L_0$. Accordingly, if the construction of the objective lens $L_0$ and the desired size $y_2$ of the fundus image are determined, the total focal length $f_{12}$ of the relay lens system necessary therefor may be obtained from equation (16).

As the basic condition of the present invention, the condition for the first lens $L_1$ is given by equation (14) and therefore, from this and equation (16), the values of $f_2$, $l_2$, $l_3$ may be obtained as follows, to complete a specific construction.

$$f_2 = -\frac{f_1 \cdot f_{12}}{\beta_0 f_0}$$
$$l_2 = f_1 - \frac{f_1}{\beta_0 \cdot f_0}(f_{12} - f_1)$$
$$l_3 = f_2$$

In such a construction, the relationship between the diopter of the eye to be examined and the amount of movement $x$ of the second lens $L_2$ is expressed as follows, and diopter correction is effected by moving the second lens $L_2$ so as to satisfy this equation.

$$(\beta_0 f_0)^2 \cdot D \cdot x^2 + (\beta_0 \cdot f_1)^2 \cdot x \cdot (f_1 \cdot f_{12})^2 \cdot D = 0 \qquad (17)$$

Also, the actual size $y_2$ of the fundus image at this time is given by the previously mentioned equation (15).

Figure 2:
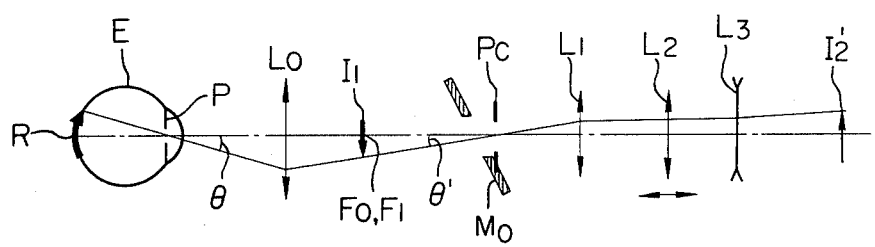
FIG. 2 shows the optical system of FIG. 1 with a negative lens added rearwardly on the relay lens.

The construction shown in FIG. 2 includes a negative lens $L_3$ disposed behind the relay lens system comprising the first lens $L_1$ and the second lens $L_2$ in the construction shown in FIG. 1. Diopter correction is possible with the previously described construction, but actually the addition of a negative lens rearwardly of the second lens $L_2$ facilitates the aberration correction of the optical system, particularly, correction of the curvature of field. Also, by the addition of a negative lens $L_3$, the position and size of the fundus image $I'_2$ are both varied as shown in FIG. 2. Therefore, by varying the focal length of the negative lens $L_3$, the size of the fundus image $I'_2$ can be varied. Or by adding a positive lens, the size of the fundus image can also be varied as desired.

The construction satisfying equation (14) permits the case where the value of $l_1$ is negative and the case where the value of $l_1$ is positive, namely, the case where the first lens $L_1$ is positive forwardly of the diaphragm $M_o$ and the case where the first lens $L_1$ is positioned rearwardly of the diaphragm $M_o$. However, generally, the diaphragm $M_o$ is an apertured mirror for the illuminating optical system, as already noted, and illuminating light is supplied to the eye E to be examined through mirror $M_o$ and therefore, if the first lens $L_1$ is disposed forwardly of the diaphragm $P_C$, flare occurs there to make it difficult to observe the eye fundus well. It is therefore desirable to dispose the first lens $L_1$ rearwardly of the diaphragm $P_C$, namely, to construct such that the value of $l_1$ is positive.

According to the eye fundus observing optical system of the present invention, as has hitherto been described, diopter correction of the inner focus type can be accomplished by a very simple construction in which a relay lens system is formed by two first and second lenses and the second lens is moved in the direction of the optic axis. Therefore, the use of the optical system of the present invention leads to the provision of an eye examining apparatus whch is compact and light in weight and easy to operate.

Where the above-mentioned equation (14) is strictly satisfied the absolute values of the amounts of forward and rearward movements of the second lens $L_2$ necessary for the positive diopter of the eye to be examined and for the negative diopter whose absolute value is equal to the positive diopter become equal to each other and the amounts of variations in size of the image become equal to each other because of equatio (15). Of course, in this case, the greatest ease of operation is provided, but it is sometimes impossible to construct the system so as to fully satisfy equation (14) due to circumstances such as its combination with the illuminating optical system and the construction of the lens barrel. In these cases, the amounts of movement of the second lens $L_2$ for the positive diopter and the negative diopter are localized forwardly and rearwardly and the amount of variation in size $y_2$ of the fundus image $I'_2$ becomes somewhat greater, but if it is within a range permissible for the observation or photography of the eye fundus, it is sufficient for actual use and does not depart from the scope of the present invention.

I claim:

1. An optical system for observing therethrough the fundus of an eye to be examined and performing diopter correction by movement of a single lens group, comprising:

an objective lens for forming a first image of the fundus of the eye to be examined;

a diaphragm member disposed at a position conjugate with the pupil of the eye with respect to said objective lens;

a relay lens system for forming a second fundus image from the first fundus image formed by said objective lens, said relay lens system being disposed at the exit side of said diaphragm member and including a first positive lens group and a second positive lens group disposed at the exit side of said first positive lens group, said first positive lens group having the entrance side focal point thereof disposed in coincidence with the exit side focal point of said objective lens, said second positive lens group being disposed at such a reference position that the entrance side composite focal point of said relay lens system may coincide with the position of said diaphragm member, said second lens group being supported for movement in the direction of the optic axis about said reference position whereby diopter correction may be performed by movement of said second positive lens group alone.

2. An optical system according to claim 1, wherein said relay lens system further has a lens group for varying the size of the second fundus image.

3. An optical system according to claim 1 or 2 further comprising an apertured mirror obliquely disposed adjacent to said diaphragm member for directing illuminating light to the eye to be examined.

* * * * *